United States Patent [19]

Vardimon et al.

[11] Patent Number: 5,752,832

[45] Date of Patent: May 19, 1998

[54] METHOD AND APPARATUS FOR MEASURING TOOTH TIGHTNESS

[75] Inventors: Alexander Vardimon, Glenview, Ill.; Tamar Brosh, Ramat Gan; Mousa Labeeb, Nazareth, both of Israel

[73] Assignee: Ramot University Authority for Applied Research & Industrial Development Ltd., Tel Aviv, Israel

[21] Appl. No.: 624,553

[22] PCT Filed: Oct. 17, 1994

[86] PCT No.: PCT/US94/11783

§ 371 Date: Apr. 3, 1996

§ 102(e) Date: Apr. 3, 1996

[87] PCT Pub. No.: WO95/10988

PCT Pub. Date: Apr. 27, 1995

[30] Foreign Application Priority Data

Oct. 19, 1993 [IL] Israel ......................................... 107325

[51] Int. Cl.$^6$ ........................................................ A61C 5/00
[52] U.S. Cl. .................. 433/215; 433/68; 433/72; 73/760; 73/774; 33/514
[58] Field of Search .................. 433/68, 71, 72, 433/215, 229, 141; 33/513, 514; 73/760, 774, 777, 778, 779, 780, 862.632

[56] References Cited

U.S. PATENT DOCUMENTS

| 984,040 | 2/1911 | Siverling ........................... 33/514 |
| 1,233,131 | 7/1917 | Schwartz ........................... 33/514 |
| 4,649,752 | 3/1987 | Turner ............................. 73/760 |
| 4,664,627 | 5/1987 | Kyotani et al. |

OTHER PUBLICATIONS

Southard, T.S. et al. "The Anterior Component of Occusal Force, Part 1. Measurement and Distribution", Am J. Orthod. Dentofac. Orthop. (1989); 96 pp. 493–500.

Southard, T.S. et al. "The Anterior Component of Occusal Force, Part 2. Relationship With Dental Malalignment", Am J. Orthod. Dentofac. Orthop. (1990); 97 pp. 41–44.

Primary Examiner—Nicholas D. Lucchesi
Attorney, Agent, or Firm—Mark M. Friedman

[57] ABSTRACT

According to the present invention there is provided an instrument for measuring the tightness between a first and a second contiguous bodies, the first body being movable with relation to the second body, comprising: (a) a substantially incompressible insertion element of predetermined thickness for insertion between the first and second bodies; (b) a holder for holding the insertion element to enable the insertion element to be forcibly inserted between the first and second bodies, thereby displacing the first body with relation to the second body, thereby providing a predetermined forced distance between the first and second bodies; and (c) a sensor for sensing the insertion force applied when inserting the insertion element between the first and second bodies along a predetermined path of insertion. Further according to the present invention there is provided a method of measuring the tightness between a first and a second contiguous bodies, the first body being movable with relation to the second body, comprising the steps of: (a) forcibly inserting a substantially incompressible insertion element of predetermined thickness between the first and second bodies; and (b) simultaneously measuring the insertion force required for displacing the first body with relation to the second body so as to provide a predetermined forced distance between the first and second bodies, wherein said measuring is performed along a predetermined path of insertion by means of a sensing element.

22 Claims, 4 Drawing Sheets

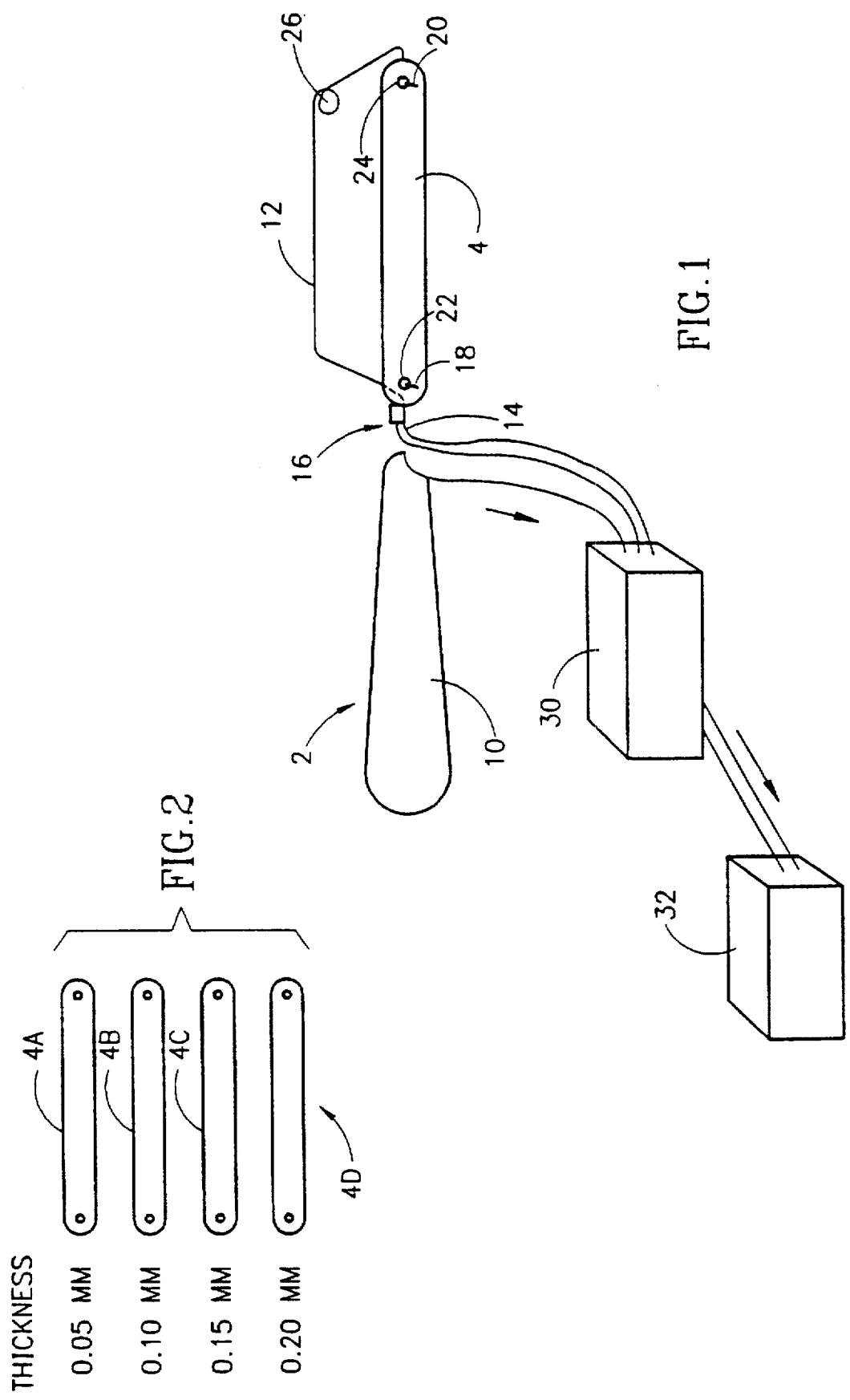

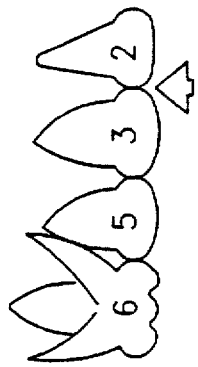
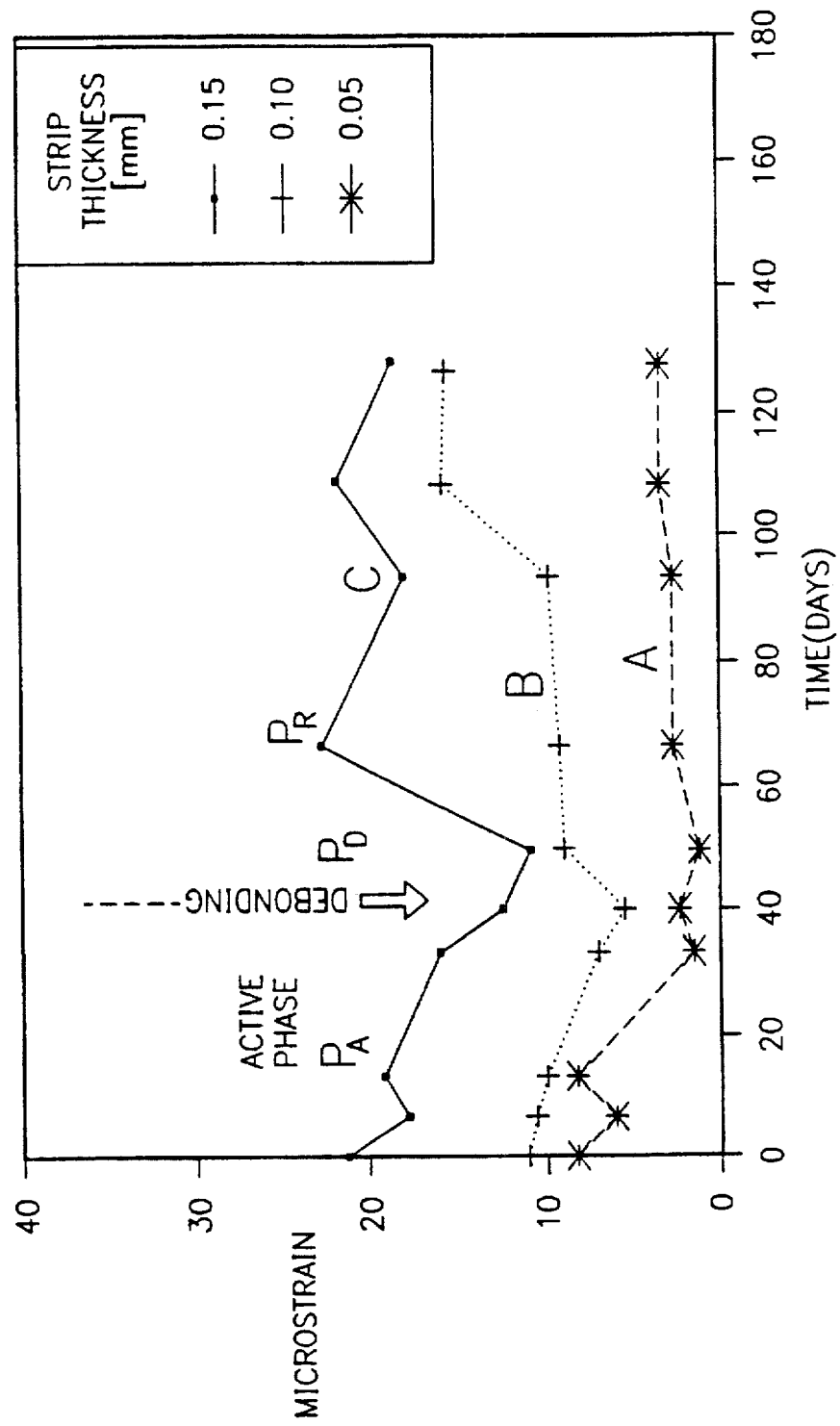
FIG.3

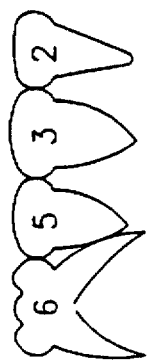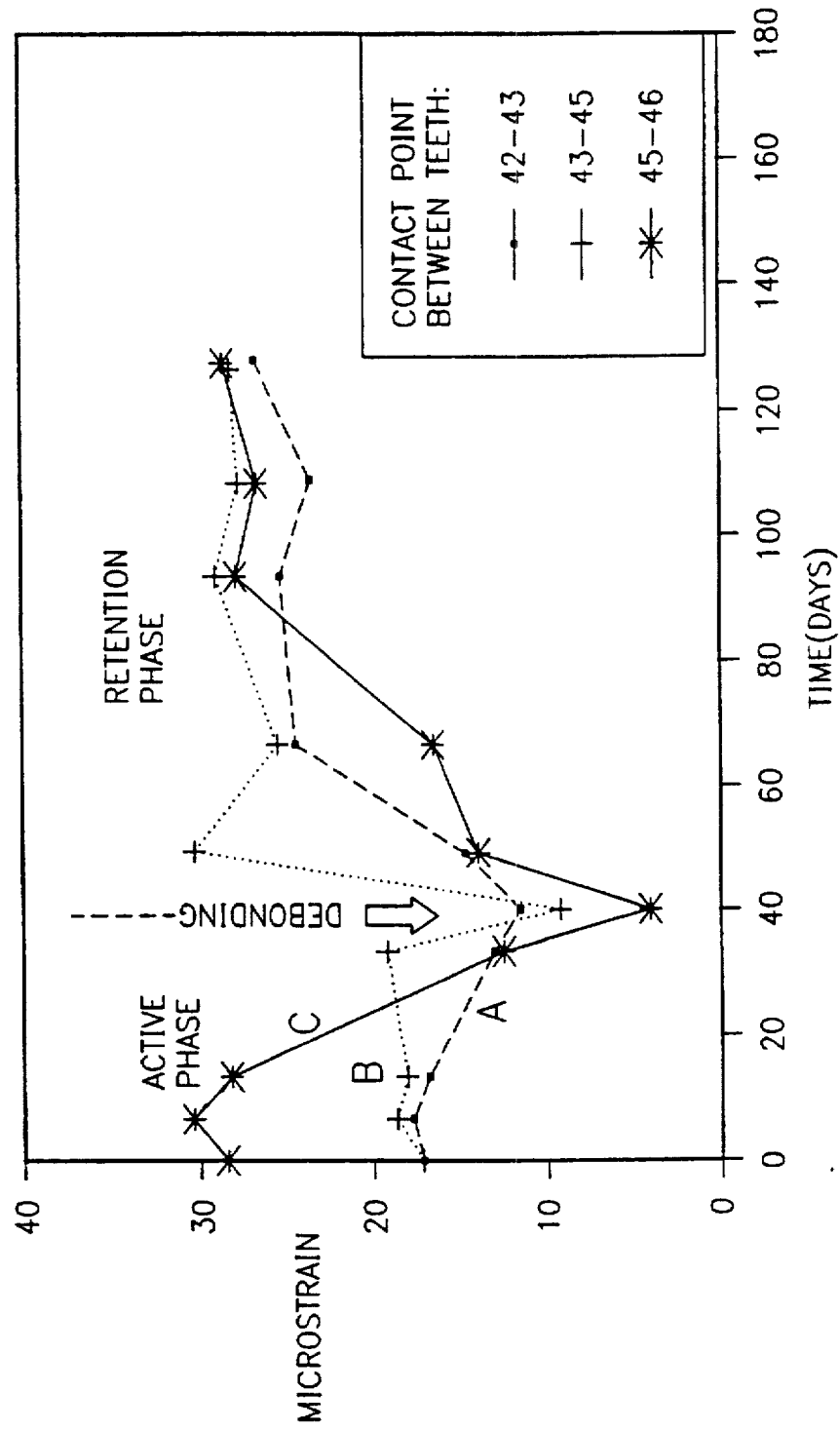
FIG. 4

METHOD AND APPARATUS FOR MEASURING TOOTH TIGHTNESS

The present invention relates to a method and also to an apparatus for measuring the tightness between two contiguous bodies. The invention is particularly useful for measuring the tightness of contiguous dental bodies, such as dental teeth, and are therefore described below with respect to this application, it being understood that the method and instrument according to the present invention is not limited to dental applications.

In the fields of orthodontics, periodontics and oral rehabilitation, there are many instances where it is desirable to measure the tightness (including looseness or spacing) between two contiguous teeth. For example at the end of an orthodontic treatment, removable retentive appliances are placed in the mouth to maintain the accomplished result. The wearing time of the retentive appliances is successively reduced until a steady state of the oral tissue is achieved. However, the extent of this recovery process is individual, and therefore if the recovery process is not monitored, there is a danger of a relapse to or towards the original condition which was to be corrected. A similar situation arises when a crown installed over a metal implant embedded in the alveolar bone, since an excessively tight contact point between a crown linked to the implant and an adjacent tooth can lead to a collapse of the bony bearing system.

U.S. Pat. No. 4,571,181, and 4,664,627 describe mechanical type dental thickness gauges for measuring the spacing between teeth, but such mechanical gauges are relatively inaccurate and generally unsuitable for use in continuously monitoring a recovery process, such as described above. A publication by Thomas E. Southard et al., entitled "Anterior Component of Occlusal Force, Part 1—Measurement and Distribution, Am. J. Orthod. Dentofac. Orthop., December 1989, pp. 439–500, describes, for this purpose, the use of a stainless steel strip slipped between the two teeth and withdrawn by the use of a digital tension transducer to measure the frictional force resisting the withdrawal of the strip.

An object of the present invention is to provide another method and instrument for measuring the tightness of two contiguous bodies, particularly dental teeth.

According to the present invention, there is provided a method of measuring the tightness of two contiguous bodies by forcibly inserting an insertion element of predetermined thickness between the two bodies; and simultaneously measuring the insertion force, preferably including the peak of the insertion force. As indicated earlier, the novel method is particularly useful for measuring the tightness of dental teeth, e.g., to permit continuous monitoring of the recovery process of an orthodontic treatment. The invention thus provides a diagnostic tool to predict hazardous side effects such as tissue relapse.

According to further features in the described preferred embodiment, the insertion element is forcibly inserted between the two teeth by attaching the opposite ends of the insertion element to a holder, and manually forcing the holder, with the insertion element attached thereto, inwardly between the two teeth towards the gingiva. In addition, the insertion element is a strip of predetermined thickness, preferably of stainless steel.

The peak of the insertion force is preferably measured by one or more strain gauges. It is possible, however, to measure the peak insertion force by measuring displacement by an optical system, a piezoelectric device, capacitance, inductance, potentiometer, or by pneumatic device, a manometer pressure device, or by the Hall effect.

It will thus be seen that the novel method of the present invention distinguishes over that in the Southard et al. publication in a number of important respects. Thus, the technique proposed by Southard et al. (Southard, T. E., Behrents, R. G., Tolley, E. A., The Anterior Component of Occlusal Force, Part 2, Relationship with Dental Malalignment, Am. J. Orthod. Dentofac. Orthop. 97; 41–4, 1990), is based on the insertion of a stainless steel strip between two teeth and the subsequent drawing of the strip laterally between the two teeth. It is during this lateral drawing that tension measurements are made. The measurements are thus primarily a combination of the tightness of adjacent teeth and the frictional forces resisting the lateral withdrawal of the steel strip. Therefore, the friction between the teeth, which is often influenced by extraneous factors, such as the presence of food particles, plaque, calculus and saliva, largely influences the tension reading and tends to mask the true tightness, thus making it impossible to distinguish between the true effect (pure tightness) and the hiss (friction).

By contrast, the present invention, involves the forcible insertion of the insertion elements between two teeth and the simultaneous measuring of the insertion force. The measurements are thus related more directly to the prying or wedging apart of the two teeth and are thus more closely related solely to the tightness of the two teeth.

Furthermore, in the Southard method, the teeth are first moved apart and then try to approach each other and thereby applying force on the insertion element. However, the very act of inserting an insertion element between a pair of teeth tends to temporarily loosen the periodontal fibers which connect the teeth to the supporting bone. Because the periodontal fibers have viscoelastic properties they will resort to their original shape after an undetermined time. Thus, during the lateral drawing of the strip in the Southard method the teeth are already considerably looser than they were prior to the insertion of the strip, rendering the measurements less accurate. By contrast, under the present invention, the measurements are conducted during the initial insertion of the insertion element simultaneously with the displacement of the teeth.

The invention also provides an instrument for measuring the tightness of two contiguous bodies, particularly dental teeth, in accordance with the above method.

Further feature and advantages of the invention will be apparent from the description below.

The invention is herein described, by way of example only, with reference to the accompanying drawings, wherein:

FIG. 1 illustrates one form of measuring instrument constructed in accordance with the present invention;

FIG. 2 illustrates a set of the insertion elements or strips of different thicknesses which may be used in the instrument of FIG. 1;

FIG. 3 illustrates typical results obtained when using three of the four different insertion strips illustrated in FIG. 2 between the same contiguous teeth;

FIG. 4 illustrates results produced when using a strip of single thickness for measuring teeth tightness with respect to several pairs of teeth during different phases of orthodontic treatment;

With reference first to FIG. 1, there is illustrated one form of instrument for measuring the tightness of two contiguous bodies, particularly dental teeth, in accordance with the present invention.

Figure 5:
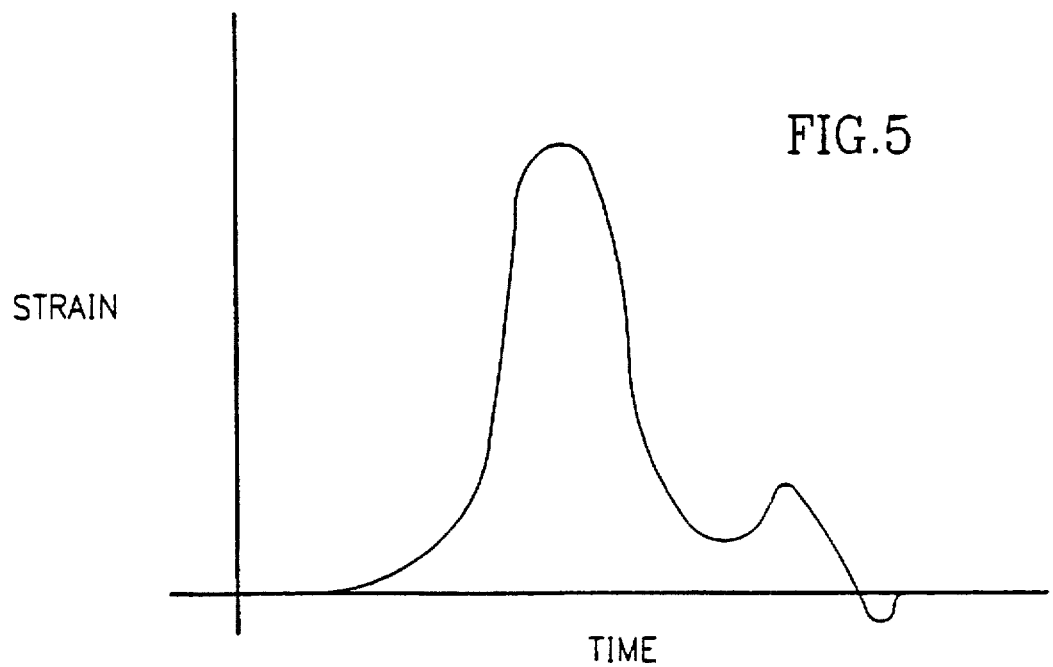
FIG. 5 is a typical strain curve.

The instrument illustrated in FIG. 1 includes a holder, generally designated 2, for holding an insertion strip 4 of predetermined thickness, such as to permit the strip to be forcibly inserted between the two dental teeth while a measurement is made of the force during the insertion or penetration between the two teeth. Preferably, the measurement includes a determination of the peak force during the insertion. An analysis of the force function, preferably including the peak of the insertion force, together with the thickness of the insertion strip 4, provide an objective indication of the tightness of the two teeth such that the tightness can be accurately measured, not only before and during the orthodontic treatment, but also after the treatment to monitor the recovery process in order to determine the stability of the results and to predict any relapse tendency in order to take whatever corrective action may be necessary to preserve the treatment results. A typical insertion force function is represented in FIG. 5. Here, the insertion force increases as the insertion element is pushed downward or upward between two adjoining teeth (or other bodies). The force peaks and then drops off again. A slight increase is typically observed when the insertion member impacts the gums. Negative tightness units are recorded when the strip is pulled out of the contact point of adjacent teeth.

Holder 2 includes a manually-graspable handle 10 mounting a U-shaped frame member 12 to which the opposite ends of the insertion strip 4 are attached. The juncture 14 between the handle 10 and the U-shaped frame 12 includes one or more strain gauges 16 which measures the strain, which is related to the insertion force, at the time strip 4 is forcibly inserted between the two teeth in order to measure the tightness thereof.

The U-shaped frame 12 is constituted of a rod bent into a U-shape and terminating in end extensions 18, 20 which are received within openings 22, 24 formed in the opposite ends of the insertion strip 4. Thus, end extensions 18, 20 of the U-shaped frame serve as attaching elements receivable within openings 22, 24 of the strip 4 for firmly attaching the strip to the U-shaped frame 12. To facilitate attaching strip 4, the frame is formed with a loop 26 providing flexibility to the end 24 of the frame, enabling that end to be engaged in the hole 24 of the strip 4.

Figure 6:
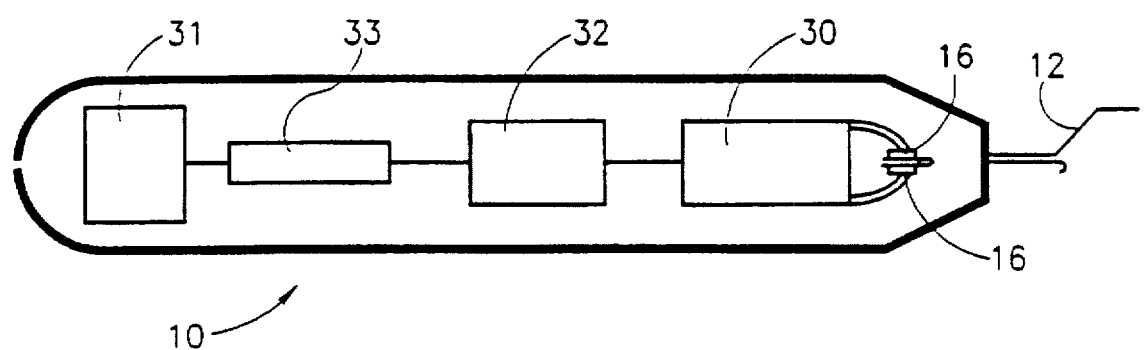
FIG. 6 shows an embodiment of a device according to the present invention.

Strain gauge 16, which senses the insertion force when inserting strip 4 between two teeth, is connected to a measuring circuit 30 for measuring the force function, preferably including at least the peak insertion force, and also to a data acquisition system 32 for processing, recording and/or displaying the measured insertion force. Preferably, the measuring circuit 30 (which may be a Wheatstone Bridge) and the data acquisition system 32 are housed within the handle 10 for ease of use of the device. The handle 10 (FIG. 6) preferably also includes a power supply 31 and preferably also a suitable display 33 for displaying the results to the user.

The one or more strain gauges 16 may be located outside of the handle 10 (as in FIG. 1) or may alternatively be located within the housing 10 (as in FIG. 6), the latter configuration offering added protection and reliability to the strain gauges 16 but requiring that the U-shaped frame member 12 and the insertion strip 4 be handled as a single item, i.e., that the combination of the U-shaped frame 12 and the insertion strip 4 be changed when desired, rather than changing merely the insertion strip 4 as in the embodiment of FIG. 1.

As indicated earlier, the insertion force depends to a great extent on the thickness of the insertion strip 4. For this reason, the instrument would be provided with a plurality of such insertion strips of different thicknesses. This is illustrated in FIG. 2, wherein, for purposes of example, strip 4a is of 0.05 mm, strip 4b is of 0.10 mm, strip 4c is of 0.15 mm and strip 4d is of 0.20 mm.

The manner of using the instrument illustrated in FIGS. 1 and 2 will be apparent from the above description.

Thus, when instrument is to be used for measuring teeth tightness, a strip 4 of suitable thickness is selected according to the particular case and is attached to the ends 18, 20 of the U-shaped frame 12. Handle 10 of the instrument is manually grasped with the strip 4 aligned in the space or contact point between the two teeth, and is pressed firmly towards the subject's gingiva to cause the strip 4 to be inserted or penetrate between the two teeth. The force required to do this is sensed by the strain gauge 16, which outputs an electrical signal to the measuring circuit 30. Circuit 30 measures the insertion force, preferably including the peak insertion force, and feeds this information to the data acquisition circuit 32, which records, displays and/or otherwise processes this information.

FIG. 3 illustrates the results of using the instrument illustrated in FIGS. 1 and 2 during a typical orthodontic treatment involving an active phase Pa during which a fixed orthodontic appliance was applied to the subjects teeth, a deboning phase Pd when the fixed orthodontic appliance was removed, and a retention phase Pr during which a removable retention appliance was applied. In the example illustrated in FIG. 3, the insertion strip 4 was applied between the same two teeth, i.e., at the same single contact point indicated by the arrow 40 in the upper right hand corner of FIG. 3. Curve A in FIG. 3 indicates the microstrain (in arbitrary tightness units) over the indicated period of time when the insertion strip 4 was strip 4a in Fig. 22, of 0.05 mm; curve B indicates the results when the insertion strip was 4b in FIG. 2, namely 0.10 mm; and curve C illustrates the results when the strip 4c, namely 0.15 mm was used.

FIG. 4 illustrates further typical results when a strip thickness of 0.15 mm was used at three contact points: teeth 2, 3; 3, 5; and 5, 6 of the fourth quadrant (right mandibular dentition). Thus, curve A shows the results when the measurement was made between teeth 2 and 3; curve B shows the results when the measurement was made between teeth 3 and 5 (teeth 4 having been removed); and curve C shows the results when the measurement was made with respect to teeth 5 and 6. The drop in the measurement indicated by the arrow (FIG. 4, contact point 45–46) is due to the removal of a band which was wrapped around the tooth 46. Due to the thickness of the band a gap was produced between the adjacent teeth which caused the sharp drop in the tightness.

While the invention has been described with respect to one preferred embodiment, it will be appreciated that this is set forth merely for purposes of example. Thus, other force measuring system could be used, for example by an optical system for measuring displacement, a piezoelectric system for measuring pressure changes, a capacitance, inductance or resistor-potentiometer system for measuring displacement. The measurement could also be pneumatically, by a manometric pressure device, or by the magnetic Hall effect.

In addition, other means can be provided for attaching the insertion strips 4 to the instrument, e.g., arrangements for attaching blades to hacksaws or jigsaws. Also, a single holder can hold a plurality of such insertion strips each made selectively operable. Further, the invention could be advantageously used for measuring tightness between other bodies.

Many other variations, modifications and applications of the invention will be apparent.

What is claimed is:

1. A method of measuring the tightness between a first and a second contiguous bodies, the first body being movable with relation to the second body, comprising the steps of:
   (a) forcibly inserting a substantially incompressible insertion element of predetermined thickness between the first and second bodies; and
   (b) simultaneously measuring the insertion force required for displacing the first body with relation to the second body so as to provide a predetermined forced distance between the first and second bodies, said predetermined forced distance being substantially equal to said predetermined thickness of said insertion element, wherein said measuring is performed along a predetermined path of insertion by means of a sensing element.

2. A method according to claim 1, wherein said measuring the insertion force includes measuring the peak of the insertion force.

3. The method according to claim 1, wherein said first and second contiguous bodies are first and second dental teeth.

4. The method according to claim 3, wherein said insertion element is forcibly inserted between the first and second teeth by attaching the insertion element to a holder, and manually forcing the holder, with the insertion element attached thereto, inwardly between the first and second teeth towards the gingiva.

5. The method according to claim 1, wherein said insertion element is a strip of predetermined thickness.

6. The method according to claim 5, wherein said strip is of stainless steel.

7. The method according to claim 1, wherein at least one of the first and second bodies is flexible.

8. The method according to claim 1, wherein at least one of the first and second bodies is connected to a flexible substrate.

9. An instrument for measuring the tightness between a first and a second contiguous bodies, the first body being movable with relation to the second body upon insertion of said instrument therebetween, comprising:
   (a) a substantially compressible insertion element of predetermined thickness for insertion between the first and second bodies;
   (b) a holder for holding said insertion element to enable the insertion element to be forcibly inserted between the first and second bodies, thereby displacing the first body with relation to the second body, thereby providing a predetermined forced distance between the first and second bodies, said predetermined forced distance being substantially equal to said predetermined thickness of said insertion element, and
   (c) a sensor for sensing the insertion force applied when inserting said insertion element between the first and second bodies along a predetermined path of insertion.

10. An instrument according to claim 9, wherein said sensor senses at least the peak of the force applied when inserting said insertion element between first and second bodies along a predetermined path of insertion.

11. The instrument according to claim 9, wherein said holder comprises a manually graspable handle, and a U-shaped frame, said frame carrying a first attaching element at said first end and a second attaching element at said second end, said first attaching element for attachment to said first end of said insertion element, and said second attaching element for attachment to said second end of said insertion element.

12. The instrument according to claim 11, wherein said insertion element is a strip of predetermined thickness, said strip having first and second ends.

13. The instrument according to claim 12, wherein said strip is formed with opening at its first and second ends for attaching the strip to said attaching elements of the U-shape frame.

14. The instrument according to claim 13, wherein one of said attaching elements is movable with respect to the other parallel to the longitudinal axis of the insertion strip to facilitate attachment of the first and second ends of the insertion strip.

15. The instrument according to claim 14, wherein said frame includes a rod bent into a U-shape and formed with a loop to permit movement of said first attaching element at said first end of said frame with respect to said second attaching element at said second end of said frame to facilitate attaching of said insertion strip thereto.

16. The instrument according to claim 10, further comprising a plurality of said insertion strips of different predetermined thickness selectively attachable to said first and second ends of said U-shaped frame.

17. The instrument according to claim 12, wherein said sensor is carried at the juncture of said handle and said U-shaped frame.

18. The instrument according to claim 12, wherein said sensor is a strain gauge.

19. The instrument according to claim 11, further including a measuring circuit for measuring the force sensed by said sensor and a data processor for processing and/or recording and/or displaying said measurement.

20. The instrument according to claim 19, wherein said measuring circuit and said data processor are located in said handle.

21. The instrument according to claims 9, wherein at least one of the first and second bodies is flexible.

22. The instrument according to claim 9, wherein at least one of the first and second bodies is connected to a flexible substrate.

* * * * *